United States Patent
Conoci et al.

(10) Patent No.: US 9,394,160 B2
(45) Date of Patent: Jul. 19, 2016

(54) MICROFLUIDIC DEVICE WITH INTEGRATED STIRRING STRUCTURE AND MANUFACTURING METHOD THEREOF

(71) Applicant: STMicroelectronics S.r.l., Agrate Brianza (IT)

(72) Inventors: Sabrina Conoci, Tremestieri Etneo (IT); Paolo Ferrari, Gallarate (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 14/250,098

(22) Filed: Apr. 10, 2014

(65) Prior Publication Data
US 2014/0308738 A1 Oct. 16, 2014

(30) Foreign Application Priority Data

Apr. 12, 2013 (IT) .............................. TO2013A0299

(51) Int. Cl.
| | | |
|---|---|---|
| *B81C 1/00* | (2006.01) | |
| *B01F 11/00* | (2006.01) | |
| *B01F 13/00* | (2006.01) | |
| *B01L 3/00* | (2006.01) | |
| *C12M 1/06* | (2006.01) | |

(52) U.S. Cl.
CPC ......... *B81C 1/00198* (2013.01); *B01F 11/0082* (2013.01); *B01F 13/0059* (2013.01); *B01F 13/0091* (2013.01); *B01L 3/50273* (2013.01); *B01L 3/502707* (2013.01); *B81C 1/00166* (2013.01); *B81C 1/00182* (2013.01); *C12M 27/02* (2013.01); *B01L 2200/12* (2013.01); *B01L 2300/06* (2013.01); *Y10T 29/49009* (2015.01)

(58) Field of Classification Search
CPC ............. B01F 13/0096; B01F 13/0064; B01F 13/0059; B01F 13/0074; B81C 1/00166; B81C 1/00182; B81C 1/00198
USPC ................. 366/116, 118, 114, 113, 111, 341, 366/DIG. 4
See application file for complete search history.

(56) References Cited

U.S. PATENT DOCUMENTS

| | | | |
|---|---|---|---|
| 8,778,666 B1 * | 7/2014 | Chung ................ | B01F 13/0091 435/287.1 |
| 2004/0021185 A1 * | 2/2004 | Oberhardt ............ | H01L 23/467 257/414 |

FOREIGN PATENT DOCUMENTS

| | | |
|---|---|---|
| WO | 2012/044154 A1 | 4/2012 |
| WO | 2012/115503 A1 | 8/2012 |
| WO | 2013/051924 A1 | 4/2013 |

* cited by examiner

*Primary Examiner* — Tony G Soohoo
*Assistant Examiner* — Anshu Bhatia
(74) *Attorney, Agent, or Firm* — Seed IP Law Group PLLC

(57) ABSTRACT

A microfluidic device, comprising: a semiconductor body, having a first side and a second side, opposite to one another in a first direction; and at least one well, configured for containing a fluid, extending in the semiconductor body starting from the first side and being delimited at the bottom by a bottom surface. The microfluidic device further comprises a stirring structure integrated in the well at the bottom surface, the stirring structure including a first stirring portion coupled to the semiconductor body and provided with at least one first suspended beam configured for being moved in a second direction so as to generate, in use, agitation of the fluid present in said well.

20 Claims, 9 Drawing Sheets

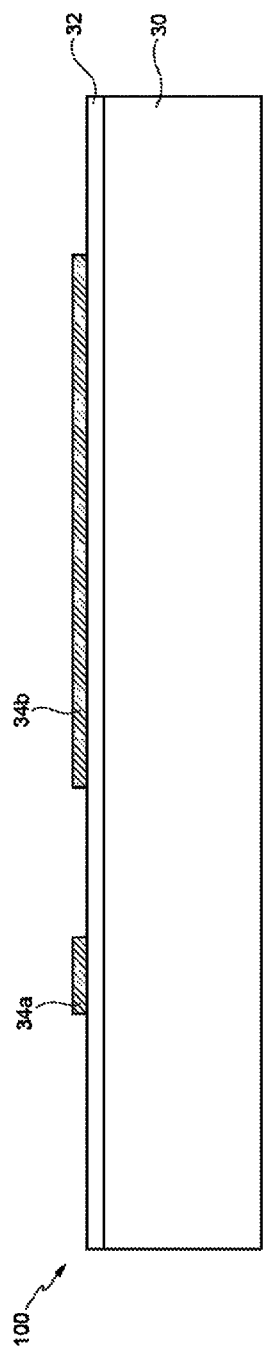
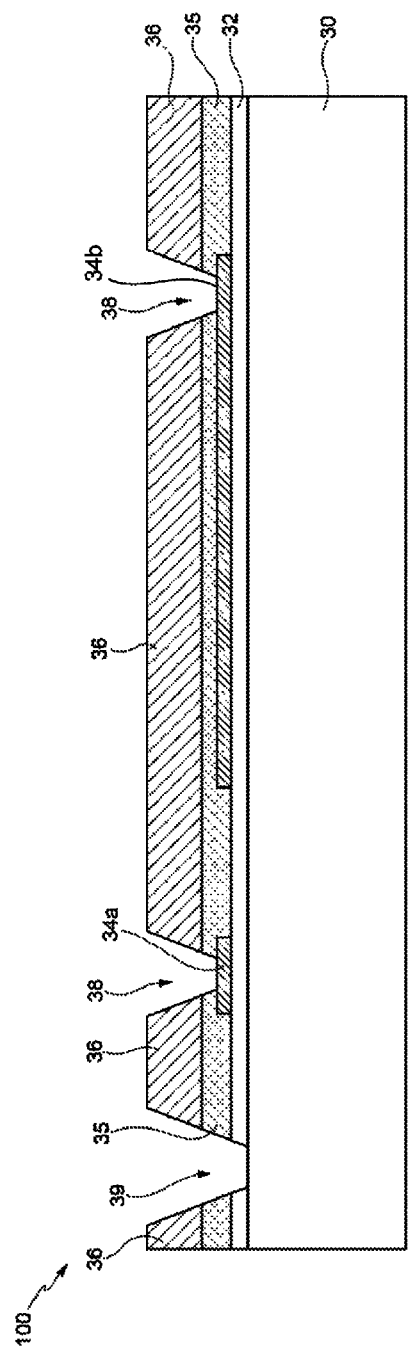
FIG. 6
FIG. 7

MICROFLUIDIC DEVICE WITH INTEGRATED STIRRING STRUCTURE AND MANUFACTURING METHOD THEREOF

BACKGROUND

Technical Field

The present disclosure relates to a microfluidic device provided with an integrated mixing or stirring structure and to a manufacturing method thereof.

DETAILED DESCRIPTION

Known to the art are various systems and methods for mixing liquids, accelerating dissolution of a solid in a liquid, favoring contact between reagents introduced in one and the same reaction chamber, and/or rendering more uniform the temperature during heating of a liquid so as to prevent local overheating. All these systems operate so as to stir the liquid in question. According to the operating situations and conditions, stirring of the liquid is obtained with different modalities, and in particular via manual or mechanical stirring. In the case of manual stirring, liquids and/or reagents to be mixed are introduced into a container (test tube, beaker, etc.) for small volumes and then, typically by means of a glass stir bar (or stirrer), they are mixed manually by an operator. The same manual operation can be carried out by shaking the test tube. In the case of automatic stirring, a small magnetic anchor, typically coated with Teflon, is put in the solution to be stirred and set in rotation by applying an external magnetic field, which, by causing rotation of the magnetic anchor, consequently generates stirring of the solution. Other stirring systems comprise supporting plates which are designed to house a plurality of containers and are configured for vibrating or rotating in a controlled way so as to favor mixing of the liquids or dissolution of the solute contained in the containers.

Other procedures for resuspending/dissolving reagents, typically used in the presence of biological molecules, comprise a first step of supplying liquid into a container pre-charged with reagents in dry/lyophilized form and a subsequent step of thermal treatment at low temperature (approximately 50° C.) for some minutes.

Irrespective of the method used, stirring of the container is obtained with the aid of a system external to the container itself, or else by manual action. In the former case, the use of external stirring systems entails the disadvantage of having to carry out the operations of stirring in the laboratory, limiting the range of use of disposable microfluidic systems. In the latter case, a manual stirring typically calls for an optimal sealing of the reaction chambers in devices that house a plurality of chambers for parallel analyses in order to prevent phenomena of cross contamination between adjacent chambers.

Moreover, mechanical stirring systems of a known type can be particularly costly.

BRIEF SUMMARY

One or more embodiments of the present disclosure is to provide a microfluidic device equipped with an integrated stirring structure and a manufacturing method thereof. One embodiment is directed to a microfluidic device that includes a semiconductor body having a first side and a second side. The device further includes a well within said semiconductor body from the first side and being delimited by a bottom surface. The well is configured to contain a fluid. The device further includes a stirring structure integrated in said well proximate the bottom surface. The stirring structure includes a first stirring portion coupled to said semiconductor body and has a first suspended beam configured to move and generate agitation of fluid in said well.

BRIEF DESCRIPTION OF THE SEVERAL VIEWS OF THE DRAWINGS

For a better understanding of the present disclosure, preferred embodiments thereof are now described, purely by way of non-limiting example and with reference to the attached drawings, wherein:

FIGS. 6-11 show in cross-sectional view steps for manufacturing a chamber provided with a stirring structure of the type shown in FIG. 2, according to one embodiment of the present disclosure.

DETAILED DESCRIPTION

According to the present disclosure, a micro-stirrer or micro-mixer is provided using MEMS technology, arranged on the bottom, or in the proximity of the bottom, of a chamber or well of a fluidic or microfluidic device.

Figure 1:
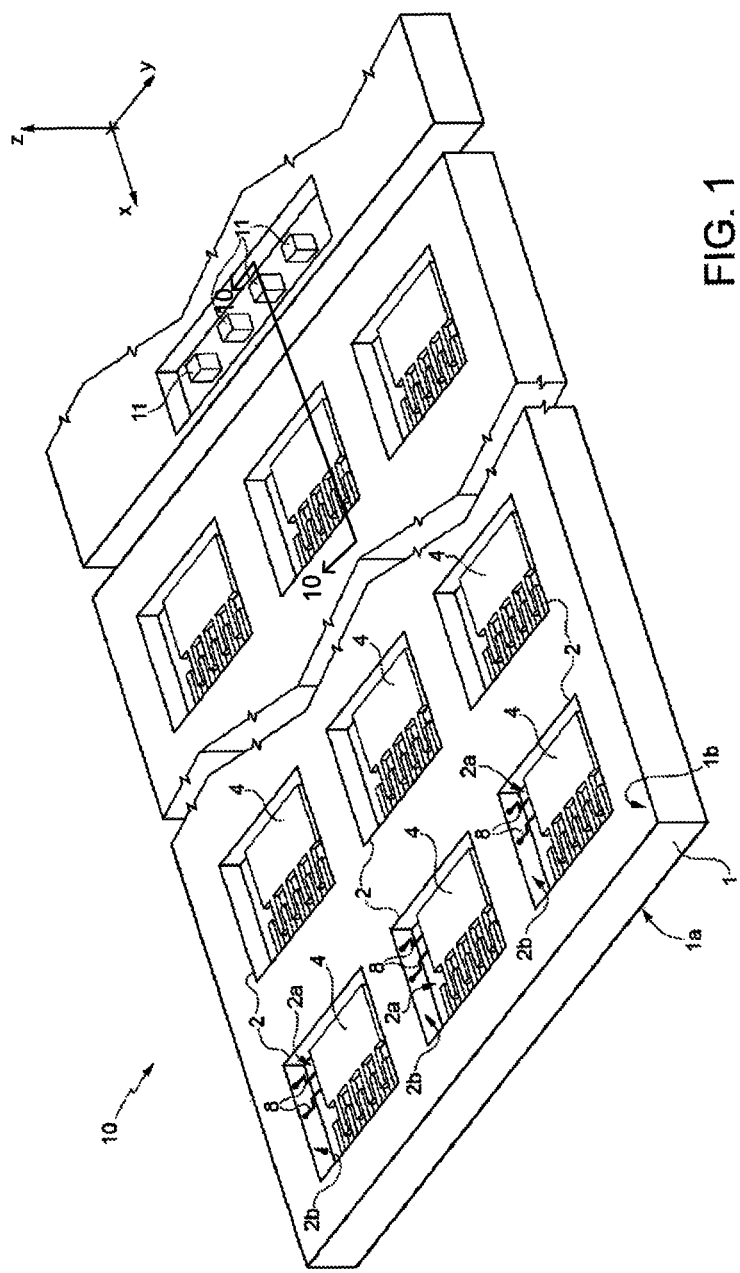
FIG. 1 shows, in perspective view and schematically, a microfluidic device including a plurality of wells provided with a respective stirring structure, according to one embodiment of the present disclosure.

FIG. 1 shows by way of example a microfluidic device 10 including a body 1, made, for example, of semiconductor material, such as polycrystalline silicon or monocrystalline silicon, having a first surface 1a and a second surface 1b opposite to one another. Even though other materials may be used for the body 1, such as plastic (for example, biocompatible plastic), glass, and ceramics, semiconductor materials are preferred for the costs and the ease of precision of manufacture, in particular using MEMS micromanufacturing techniques.

The body 1 houses a plurality of wells or chambers 2, each chamber 2 extending in depth in the body 1 (in a direction Z substantially orthogonal to the first and second surfaces 1a, 1b of the body 1) and being delimited by a bottom wall 2a and by side walls 2b. According to one embodiment, each chamber 2 extends in the body 1 for a depth, measured in the direction Z starting from the top surface 1a, comprised between 200 and 600 µm, for example, 400 µm. It is evident that said dimensions are provided by way of example of an embodiment of the present disclosure, and variants may be devised according to the preferences.

Each chamber 2 is configured for housing pre-charged reagents, typically in the solid phase (for example, lyophilized). According to one embodiment, each chamber 2 forms a micro-reactor for biochemical analyses, and the reagents are of a biological type such as, for example, DNA strands, enzymes, etc.

According to an aspect of the present disclosure, each chamber 2 moreover houses, in the proximity of its bottom wall 2a, a stirring structure 4. According to one embodiment, the stirring structure 4 includes one or more beams or fingers configured for being moved, in use, in a direction substantially orthogonal with respect to the bottom wall 2a (i.e., along Z) and/or in a direction substantially parallel to the bottom wall 2a (i.e., along X or Y).

In use, the chambers 2 are filled with a fluid in which reagents in the solid phase (for example, primers/PCR probes) are soluble (for example, said fluid is a saline solution, possibly with appropriate buffers and enzymes). The reagents in the solid phase are effectively suspended or dissolved in the fluid introduced into the chamber 2 exploiting the effect of the turbulence generated by the movement of the beams or fingers of the stirring structure 4.

It is evident that, according to other embodiments, the stirring structure 4 may include vibrating elements having shapes different from the beam or finger shape, for example generically polygonal, shaped in such a way that, when driven in vibration along Z, and/or moved in the plane XY, it will generate an action of stirring of the fluid contained in the chamber 2.

Actuation of the stirring structure takes place, according to one aspect of the present disclosure, by electrical potential applied to distinct portions of the stirring structure 4 so as to move parts thereof under the effect of an electric field. The electrical potential is applied via contact electrodes or pads 11 formed outside the chambers 2, as will be better illustrated in what follows.

Figure 2:
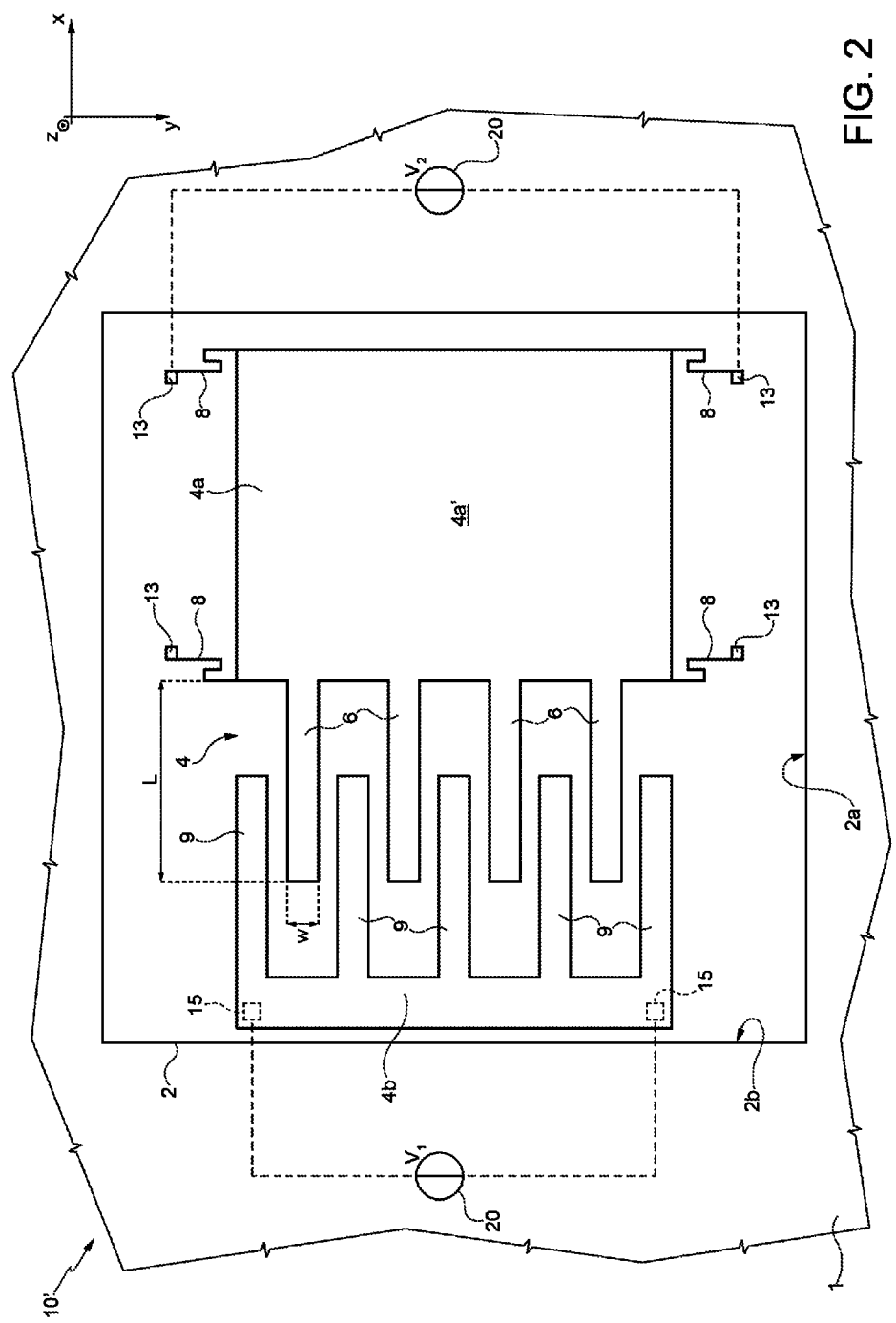
FIG. 2 shows, in top plan view, a well of the microfluidic device of FIG. 1 including a stirring structure according to one embodiment of the present disclosure.

FIG. 2 shows, in top plan view, a chamber 2 of the microfluidic device 10 of FIG. 1 provided with a stirring structure 4 that includes a comb-shaped mobile mass 4a. In particular, the mobile mass 4a comprises a plurality of elongated elements 6 that extend in cantilever fashion starting from a central body 4a' of the mobile mass 4a and that form suspended beams having a preferred direction of extension parallel to the bottom wall 2a (in particular, in FIG. 2, along X). Moreover, the mobile mass 4a includes elastic suspension and anchorage elements (springs 8) that enable coupling of the central body 4a' of the mobile mass 4a to the body 1 via anchorage regions 13, and moreover enable movement of the mobile mass 4a in a direction parallel to the bottom wall 2a (in FIG. 2, in the direction X). The stirring structure 4 further includes a fixed mass 4b, having a shape similar to the shape described and shown for the mobile mass 4a, in particular a comb shape including a plurality of elongated elements 9 that form suspended beams having a preferred direction of extension parallel to the bottom wall 2a and parallel to the preferred direction of extension of the suspended beams 6 of the mobile mass 4a (i.e., in this case, along X). The fixed mass 4b is constrained to the bottom wall 2a of the chamber 2 via respective anchorage regions 15, by means of which it is fixed with respect to the body 1.

It is evident that the number of the suspended beams 8 and 9 is chosen according to the preferences, and may vary from one (a single suspended beam 6 and a single suspended beam 9) to N, with N chosen freely, and in particular on the basis of the dimensions of the suspended beams and of the chamber 2.

The suspended beams 6 of the mobile mass 4a are interspersed or comb-fingered with the suspended beams 9 of the fixed mass 4b.

According to one embodiment of the present disclosure, each suspended beam 6 and 9 has a thickness S, measured along Z, comprised between 5 µm and 30 µm, for example 20 µm. Moreover, each suspended beam 6 and 9 has a length L, measured along X starting from the central body 4a', comprised between 50 µm and 300 µm, for example 150 µm, and a width W, measured along Y, comprised between 20 µm and 10 µm, for example 15 µm.

Through the anchorage regions 13, the mobile mass 4a can be biased at a biasing voltage V1, for example equal to a ground reference value GND (approximately 0 V). Through the anchorage regions 15, the fixed mass 4b can be biased at a biasing voltage V2, for example oscillating around a mean value and configured for assuming a peak value comprised (in modulus) between approximately 20 V and a value $V2_{max} > 20$ V.

The voltage value $V2_{max}$ is chosen in such a way that the leakage current $i_{LEAK}$, due to the presence of a possible conductive fluid in contact with the mobile mass 4a and the fixed mass 4b, is much smaller than the biasing current used for biasing the fixed mass 4b to the voltage value $V2_{max}$. In particular, the value of the biasing current corresponding to the voltage value $V2_{max}$ is greater by approximately two orders of magnitude than the leakage current $i_{LEAK}$. By way of example, if $i_{LEAK} \approx 1$ µA, then the biasing current corresponding to the voltage value $V2_{max}$ is approximately 100 µA.

From a practical standpoint, if the conductive characteristics of the fluid introduced into the chamber 2 are not known, after having set the voltage V1 to the reference value GND, the voltage V2 can be increased up to an operating value $V_O$ such that there is noted a movement of the mobile mass 4a (or of mobile portions thereof). Said operating value $V_O$ can hence be chosen as value of biasing of the fixed mass 4b when the aforementioned fluid is introduced into the chamber 2.

The biasing voltages V1 and V2 are generated by a driving unit 20 that can be electrically coupled to the anchorage regions 13 and 15 and is configured for generating driving voltages V1 and V2 variable in time and, hence, identified hereinafter by the notation V1(t) and V2(t), respectively.

Figure 3A:
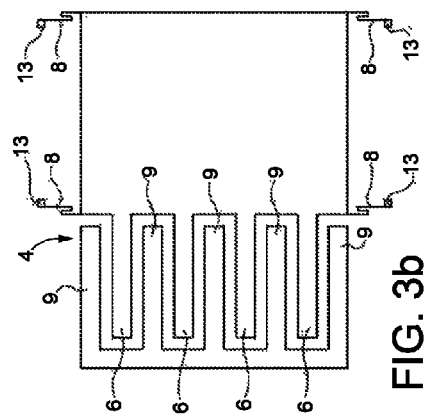
FIGS. 3a-3d show the well of FIG. 2 in different operating conditions according to the present disclosure.
Figure 3B:
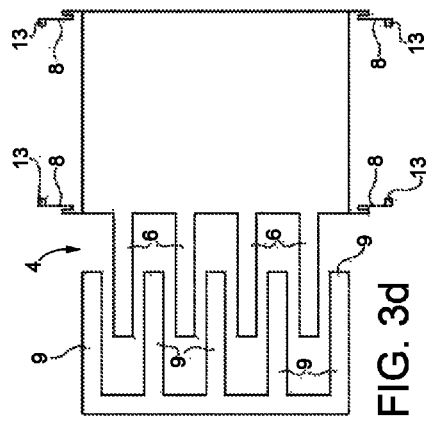

According to one embodiment (FIGS. 3a and 3b), the springs 8 are configured in such a way that, in a resting condition, they maintain the suspended beams 6 of the mobile mass 4a at a distance from the spatial regions comprised between mutually facing suspended beams 9 of the fixed mass 4b. In other words, in the resting condition, the suspended beams 6 and the suspended beams 9 are not comb-fingered, or are minimally comb-fingered (condition of FIG. 3a). The driving voltages V1(t) and V2(t) oscillate in phase opposition with respect to a mean constant value. The driving voltages V1(t) and V2(t) can hence be defined by the following equations $$V1(t)=Vb+Vd(t) \text{ and } V2(t)=Vb-Vd(t)$$

Where Vb is a constant biasing voltage and Vd(t) is an AC voltage, for example rectangular or sinusoidal.

Since the voltages V1(t) and V2(t) are in phase opposition, they generate between the mobile mass 4a and the fixed mass 4b a force of attraction with a frequency that is twice the frequency of the AC voltage Vd(t). Since the springs 8 are configured for enabling an oscillation or vibration of the mobile mass 4a along X, said force moves the mobile mass 4a in the direction X, approaching the mobile mass 4a to the fixed mass 4b with a frequency given by the frequency of the AC voltage Vd(t). It is evident that the voltages V1(t) and V2(t) are chosen in such a way as to generate a force sufficient to overcome the force of opposition of the springs 8 (condition of FIG. 3b). The presence of the springs 8 enables the mobile mass 4a to be brought back into the resting position (FIG. 3a) when the force generated by the voltages V1(t) and V2(t) ceases (i.e., upon zero crossing of the AC voltage Vd(t), when, that is, V1(t)−V2(t)=Vb(t)).

Figure 3C:
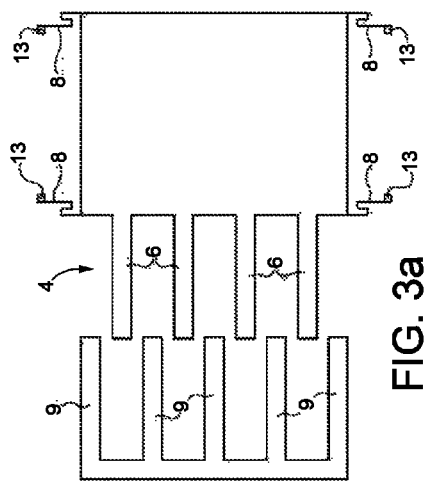
Figure 3D:
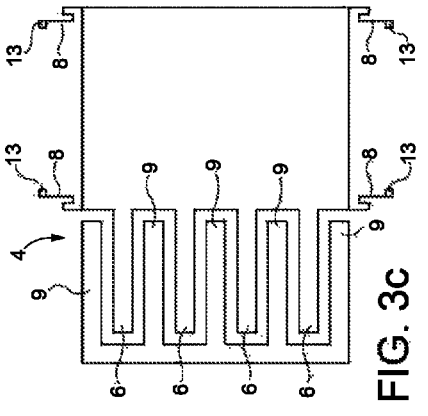

According to a different embodiment (FIGS. 3c and 3d), the springs 8 are configured in such a way that, in the resting condition, they keep the suspended beams 6 of the mobile mass 4a inside the spatial regions comprised between mutually facing suspended beams 9 of the fixed mass 4b. In other words, in the resting condition, the suspended beams 6 and the suspended beams 9 are completely comb-fingered (condition of FIG. 3c). The driving voltages V1(t) and V2(t) oscillate with one and the same phase with respect to a constant mean value. The driving voltages V1(t) and V2(t) can hence be defined by the following equations:

$$V1(t)=V2(t)=Vb+Vd(t) \text{ (or, likewise, } V1(t)=V2(t)=Vb-Vd(t)),$$

where Vb is a constant biasing voltage, and Vd(t) is an AC voltage, for example rectangular or sinusoidal.

Since the voltages V1(t) and V2(t) have the same phase, a repelling force is generated between the mobile mass 4a and the fixed mass 4b. The repelling force has a frequency that is twice the frequency of the AC voltage Vd(t). Since the springs 8 are configured for enabling an oscillation or vibration of the mobile mass 4a along X, said force moves the mobile mass 4a in the direction X, moving away the mobile mass 4a from the fixed mass 4b (condition of FIG. 3d) with a frequency given by the frequency of the AC voltage Vd(t). It is evident that the voltages V1(t) and V2(t) are chosen in such a way as to generate a force sufficient to overcome the force of opposition of the springs 8. The presence of the springs 8 enables the mobile mass 4a to be brought back into the resting position (FIG. 3c) when the force generated by the voltages V1(t) and V2(t) ceases (i.e., upon zero crossing of the AC voltage Vd(t), i.e., when V1(t)≈V2(t)=Vb(t)).

The presence of the suspended beams 6 comb-fingered to the suspended beams 9, moved as described with reference to the embodiments of FIGS. 3a and 3b, or FIGS. 3c and 3d, favors stirring of the fluid and resuspension therein of the reagents present in the chamber 2, or mixing of fluids, according to the specific application.

Figure 4:
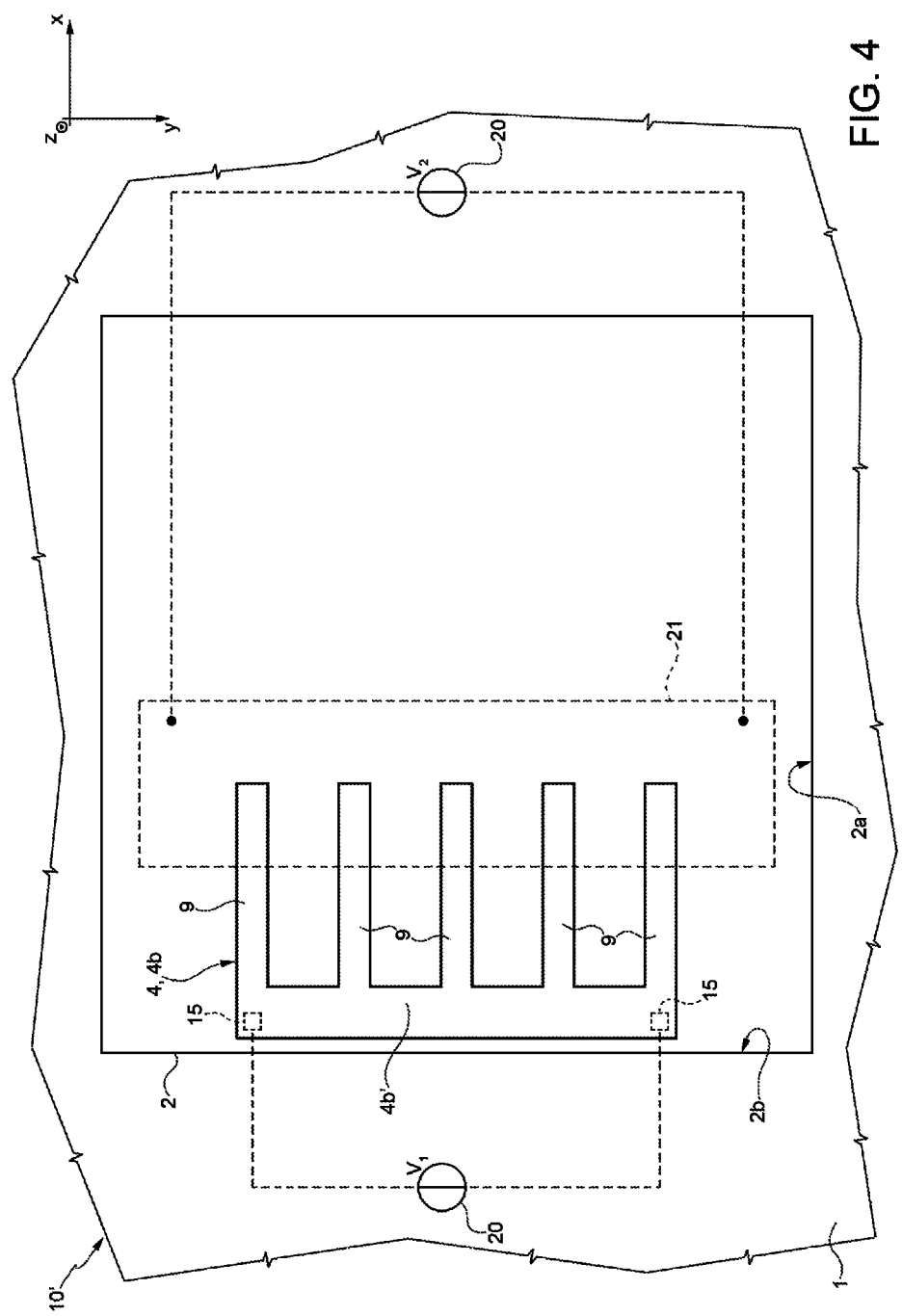
FIG. 4 shows in top plan view, a well of the microfluidic device of FIG. 1 including a stirring structure according to a further embodiment of the present disclosure.
Figure 5:
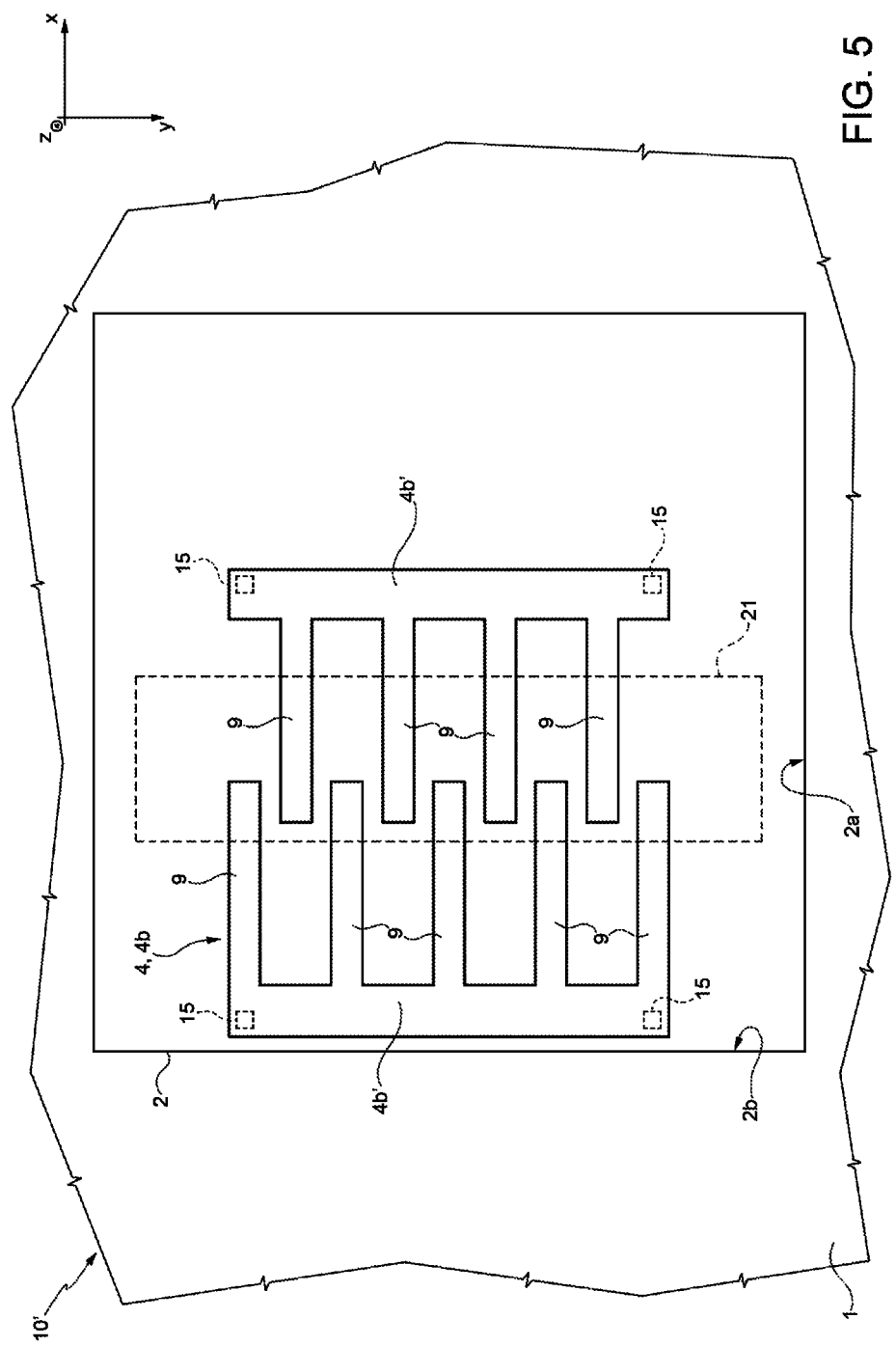
FIG. 5 shows in top plan view a well of the microfluidic device of FIG. 1 including a stirring structure according to a further embodiment of the present disclosure.

FIGS. 4 and 5 show a microfluidic device 10' comprising a chamber 2 provided with respective stirring structures 4, according to respective further embodiments of the present disclosure.

According to the embodiment of FIG. 4, the stirring structure 4 comprises the single fixed mass 4b. According to the embodiment of FIG. 5, the stirring structure 4 comprises a plurality of fixed masses 4b similar to one another and set at a distance apart from one another in the chamber 2.

With reference to FIGS. 4 and 5, moreover, extending in the proximity of the bottom wall 2a of the chamber 2 are one or more fixed electrodes 21 (just one electrode 21 is shown in FIGS. 4 and 5). The fixed electrode 21 is provided in a form integrated in the body 1 underneath the bottom wall 2a and separated from the chamber 2 by means of a portion of the body 1.

The fixed mass 4b is of the type described with reference to FIG. 2 and includes a central body 4b', having a supporting function, departing from which are the suspended beams 9, extending, as has been said, along X. The anchorage regions 15 extend in the area of, and are fixed with respect to, the central body 4b' and raise the fixed mass 4b above the bottom wall 2a by a distance (measured along Z) chosen according to the preferences and given substantially by the thickness (along Z) of the anchorage regions 15. For example, said distance is comprised between 1.3 µm and 3 µm, and in any case is of a value such as to enable a vibration along Z of the suspended beams 9 without the latter impacting, during movement, on the bottom wall 2a of the chamber 2.

Hence, the suspended beams 9 are free to move, if appropriately actuated, along Z, in both directions (i.e., approaching, and receding from, the bottom wall 2a). Said actuation is carried out by biasing appropriately the fixed electrode 21 and the fixed mass 4b, for example using the biasing voltages V1 and V2 previously described with reference to the embodiments of FIGS. 3a and 3b, or, alternatively, FIGS. 3c and 3d. For example, irrespective of the embodiment, the biasing voltage V1(t) (of a fixed value equal to the reference voltage GND or variable with a peak value around a few volts, for example 3V) is applied to the fixed mass 4b via the anchorage regions 15, and the biasing voltage V2(t) (voltage variable in time with a peak value of 20 V) is applied to the fixed electrode 21.

The fixed electrode 21 and the fixed mass 4b are hence biased by respective periodic voltages (with rectangular or sinusoidal waveform centered around a reference value) and such as to attract electrostatically the suspended beams 9 towards the fixed electrode 21 or repel electrostatically the suspended beams 9 from the fixed electrode 21. A movement along Z of the suspended beams 9 is thus created.

According to a different embodiment, the fixed electrode 21 is biased by a periodic voltage V2(t) (rectangular or sinusoidal), whereas the voltage V1 has a fixed value. The voltage V2(t) is configured in such a way that, in a first semi-period, it has a positive value $V2^+$ such that the suspended beams 9 are electrostatically attracted towards the fixed electrode 21 and, in a second semi-period immediately subsequent to the first semi-period, has a negative value $V2^-$ such that the suspended beams 9 are electrostatically repelled from the fixed electrode 21. A movement along Z of the suspended beams 9 is thus created.

FIG. 5 shows a chamber 2 where the stirring structure 4 includes two fixed structures 4b similar to one another (of the type previously described with reference to FIGS. 2 and 4), facing one another, possibly with comb-fingered or partially comb-fingered suspended beams 9. This embodiment, which includes a plurality of fixed structures 4b, enables increase in the turbulence of the fluid during actuation of the stirring structure 4 as compared to the embodiment of FIG. 4, which presents a single fixed mass 4b, further improving stirring thereof and hence dissolution/mixing of the reagents/fluids.

Figure 8:
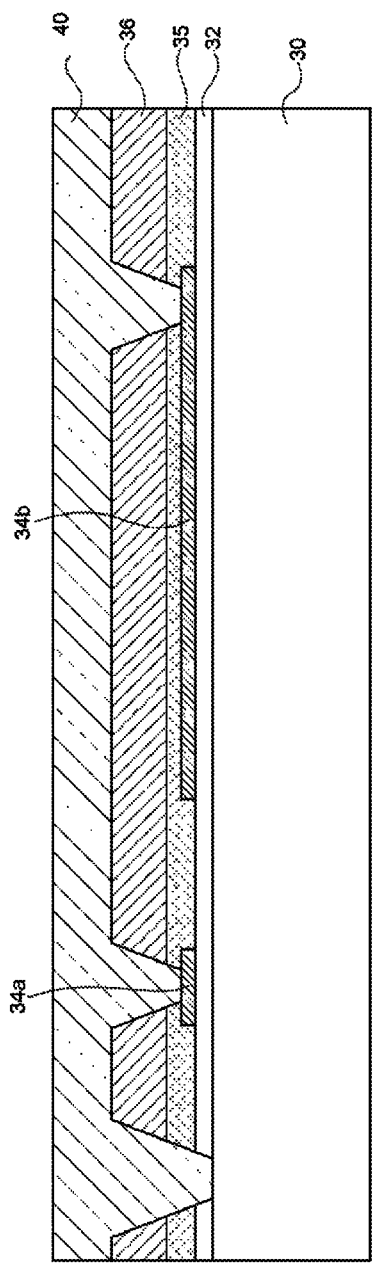
Figure 9:
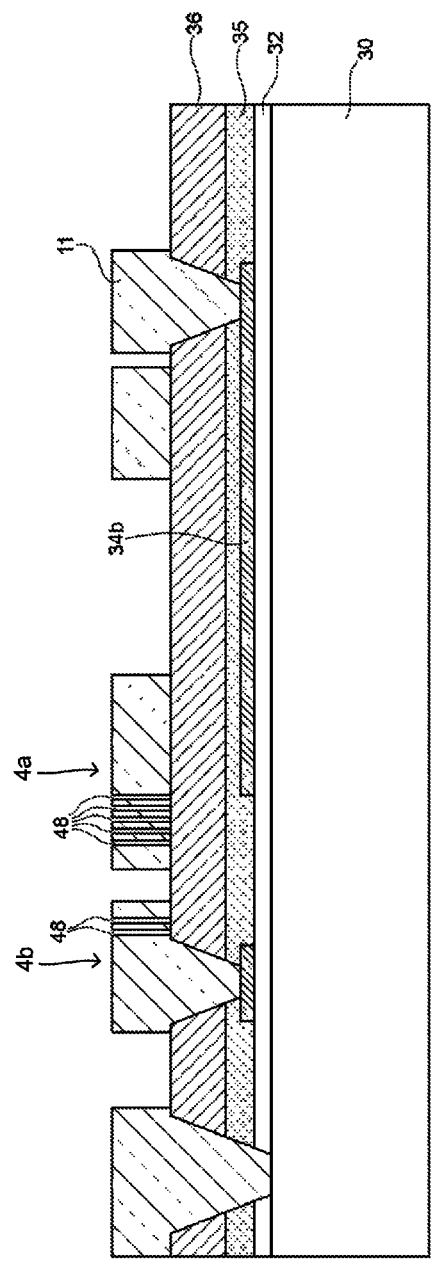
Figure 10:
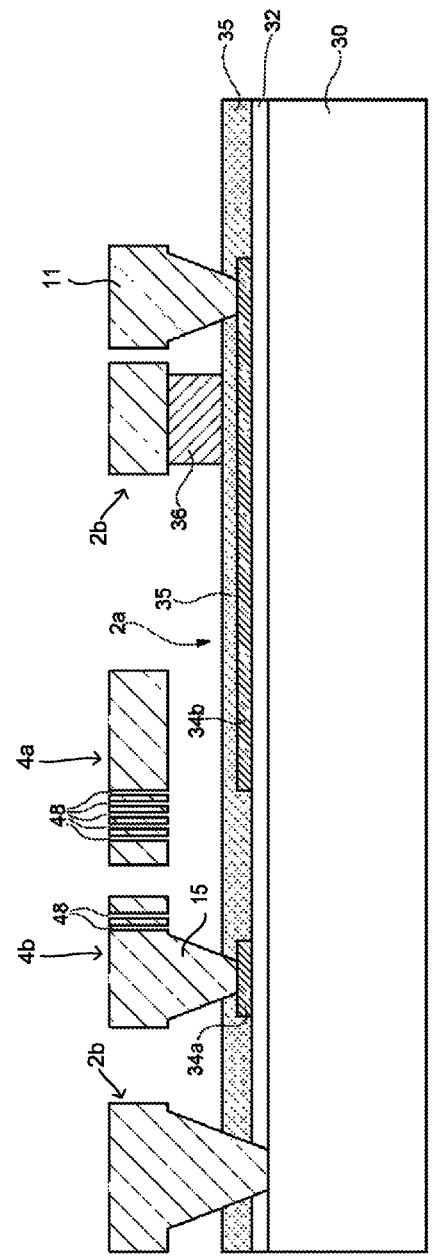

FIGS. 6-11 show, in cross-sectional view, steps for manufacturing the microfluidic device 10, in particular according to the embodiment of FIG. 2. FIG. 10 shows a cross-sectional view of the microfluidic device 10 along the axis shown in FIG. 1.

With reference to FIG. 6, a wafer 100 is provided, having a substrate 30 made of semiconductor material, for example silicon, of a thickness comprised between 400 µm and 700 µm. Then, formed on the substrate 30, is a supporting layer 32, made of silicon oxide, for example grown thermally. This supporting layer 32 is also known as "permanent-oxide layer" or "field-oxide layer", and has a thickness, for example, of between 1.5 and 3 µm approximately. The supporting layer 32 has a supporting and electrical-insulation function in regard to overlying structures (formed in the next step).

Formed on the supporting layer 32 is a layer of doped polysilicon (for example, with a doping of an N type), which is then etched so as to remove selective portions of the polysilicon layer and form electrical-contact regions 34a, 34b. The electrical-contact regions 34a, 34b are conductive strips and provide electrical interconnections through which the mobile mass 4a and the fixed mass 4b of the stirring structure 4 can be biased via the biasing voltages V1 and V2. Etching of the polysilicon layer, to form the electrical-contact regions 34a, 34b, is of a selective type and does not remove the supporting layer 32 or parts thereof. As mentioned previously, the supporting layer 32 has the function of insulating electrically the electrical-contact regions 34a, 34b from the substrate 30.

As shown in FIG. 7, formed (for example, with deposition techniques, e.g., PECVD) on the supporting layer 32 and on the electrical-contact regions 34a, 34b is an insulation layer 35, made of electrically insulating material, having a thickness comprised between 1 μm and 2 μm.

A sacrificial layer 36 is formed (for example, by deposition techniques, e.g., PECVD) on top of the insulation layer 35. The sacrificial layer 36 has a thickness comprised between 1 μm and 3 μm and defines the distance between the suspended portions of the stirring structure 4 and the bottom wall 2a of the chamber 2.

The respective materials of the insulation layer 35 and of the sacrificial layer 36 are chosen freely according to the preferences, provided that they can be etched selectively (i.e., etching of the sacrificial layer 36 does not remove or damage the insulation layer 35). For example, if a sacrificial layer 36 of 1.5 μm is used, the insulation layer is, for instance, 50 nm thick.

By means of steps of lithography and subsequent etching, portions of the sacrificial layer 36 and of the insulation layer 35 are removed in areas corresponding to respective portions of the underlying electrical-contact regions 34a, 34b to form a plurality of trenches 38 that extend up to the electrical-contact regions 34a, 34b so as to expose respective surface portions of the electrical-contact regions 34a, 34b. In particular, in FIG. 7, two trenches 38 are formed on top of the electrical-contact regions 34a, 34b.

During the step of FIG. 7, a trench 39 is moreover formed, which extends through the sacrificial layer 36, the insulation layer 35, and the supporting layer 32, until the top surface of the substrate 30 is reached and exposed. In subsequent manufacturing steps, said trench 39 provides the passage to form a ground terminal in electrical contact with the substrate 30.

As shown in FIG. 8, formed on top of the sacrificial layer 36 and into the trenches 38, 39 is a structural layer 40, for example made of epitaxial polysilicon ("EPIPoly"), which extends into the trenches 38 until it comes into electrical contact with the electrical-contact regions 34a, 34b, and into the trench 39 until it comes into electrical contact with the substrate 30. The structural layer 40 forms, in subsequent steps, the mobile structure 4a and the fixed structure 4b, and has a thickness comprised between 5 μm and 30 μm.

The structural layer 40 can be machined according to preferences in order to form structures having the desired conformation, in particular a stirring structure 4 having the desired shape, which is not limited to the one shown in FIGS. 2-5.

In FIG. 8 the electrical contact between the structural layer 40 and the electrical-contact region 34b (which, at the end of the manufacturing steps, provides the anchorage regions 13) is not shown. In any case, it is similar to, and formed together with, the contact regions between the structural layer 40 and the electrical-contact regions 34a, 34b, which extend in the trenches 38.

In FIG. 9, the structural layer 40 is etched selectively for defining the stirring structure 4, including the mobile mass 4a and the fixed mass 4b. The shape chosen for the mobile mass 4a and the fixed mass 4b (e.g., the number of suspended beams 6, 9, their shape, etc.) can be defined readily by means of an appropriate lithographic mask, in a way in itself evident to the person skilled in the branch.

In this way, both the stirring structure 4 (mobile mass 4a and fixed mass 4b) and the side walls 2b that delimit laterally the chamber 2 that houses the stirring structure 4 are formed. In particular, the chamber 2 is formed together with definition of the stirring structure 4, with evident advantages in terms of simplicity of production and reduction in costs. Simultaneously, also the springs 8 are formed, defined lithographically in the structural layer 40 together with lithographic definition of the mobile mass 4a. The springs 8 are hence made of a single piece with the mobile mass 4a and are anchored to the body 1 via anchorage pillars, which extend, as has been said, until they come into electrical contact with the electrical-contact region 34b. The mobile mass 4a, the springs 8, and the anchorage pillars are defined according to techniques of silicon machining in themselves known, for example dry etching by means of an appropriate etching mask.

Moreover formed are electrical-contact terminals 11, external to the chamber 2 (just one electrical-contact terminal 11 is shown in FIG. 4). By means of the electrical-contact terminal 11 it is possible to bias, from the outside of the chamber 2, the electrical-contact region 34b and, via the latter, the mobile mass 4a.

It should be noted, however, that in this manufacturing step the mobile mass 4a and the fixed mass 4b are still constrained and adjacent to the underlying sacrificial layer 36, and hence the mobile mass 4a is not free to perform movements.

According to the preferences, moreover formed in the fixed mass 4b and/or in the mobile mass 4a are through holes 48 for enabling removal, by means of wet chemical etching, of the sacrificial layer 36 so as to suspend partially the mobile mass 4a and the fixed mass 4b. This process step is shown in FIG. 10, where the mobile mass 4a and the fixed mass 4b are rendered suspended by removing portions of the sacrificial layer 36 that extend underneath them. Etching is of a wet type and is carried out, for example, using a solution or mixture containing hydrofluoric acid (HF).

The respective portions of the mobile mass 4a and of the fixed mass 4b that extend in the trenches 38 form respective resting bases for the mobile mass 4a and the fixed mass 4b, providing the anchorage regions 13 and 15, respectively. Said resting bases (anchorage regions 13 and 15) are moreover in electrical contact with the underlying electrical-contact regions 34a, 34b, via which they can be appropriately biased by means of electrical-contact terminals provided outside the chamber 2 (e.g., the electrical-contact terminal 11).

As may be noted from FIG. 10, the insulating layer 35 and part of the sacrificial layer 36 remain underneath portions of the side walls 2b to provide a support therefor and to guarantee an adequate electrical insulation of the side walls 2b from the electrical-contact region 34b.

In addition, since the electrical insulation layer 35 is not removed by the previous etching step, the electrical-contact regions 34a, 34b are electrically insulated from the bottom wall 2a of the chamber 2. In this way, when the chamber 2 is, in use, filled with fluid, the electrical-contact regions 34a, 34b are not in direct electrical contact with said fluid.

Figure 11:
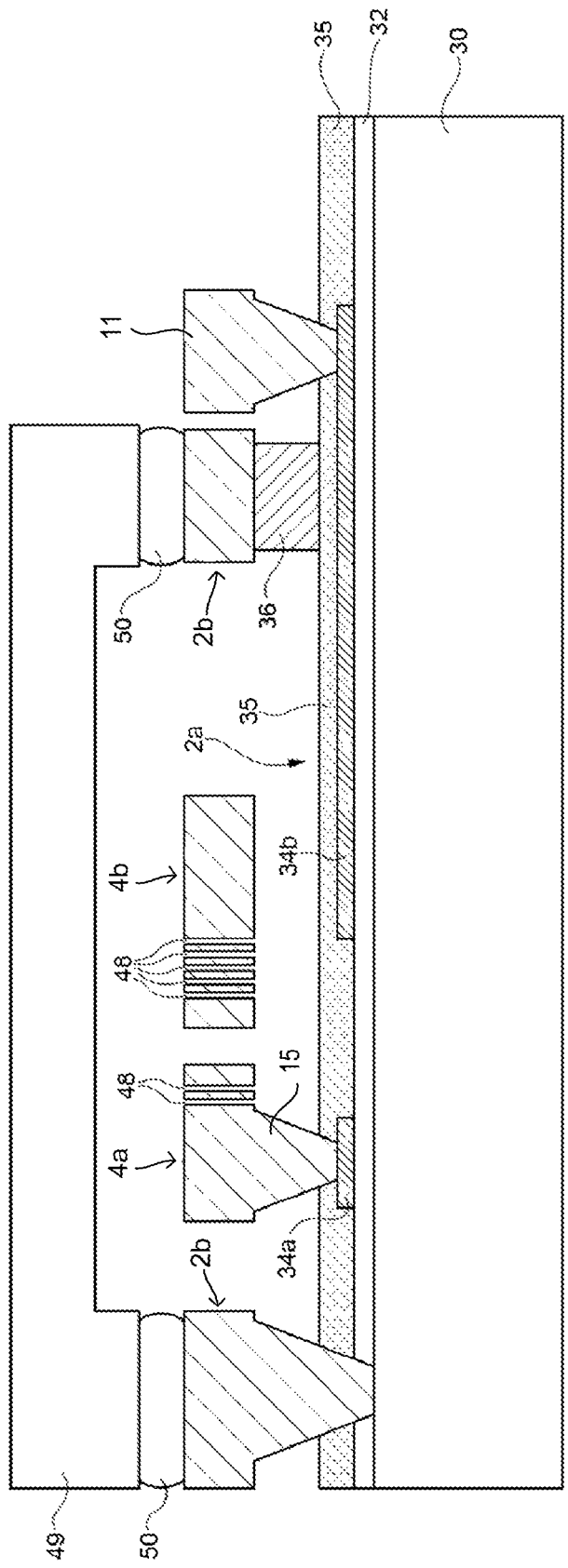

As shown in FIG. 11, manufacturing of the microfluidic device 10 (as has been said, just a portion thereof is shown) is completed by providing a cap 49 on top of, and in contact with, the side walls 2b of the chamber 2. The cap 49 and the side walls 2b are coupled together by soldering material 50, of a conductive type or else of an insulating type, according to the preferences. In this way, the chamber 2 is isolated from the external environment.

Provision of the cap 49 is optional and not necessary for the purposes of the present disclosure. In order to render the chamber 2 accessible from outside (for example, in order to introduce the aforementioned fluid), it is possible to provide one or more fluidic channels (not shown) for access to each chamber 2 belonging to the microfluidic device 10, or else, alternatively, to provide a hole for fluidic access through the cap 49 (not shown). Since said aspects do not form part of the present disclosure, they are not discussed any further herein.

In use, the mobile mass 4a can be biased at the voltage V2 by means of the electrical-contact terminal 11, accessible from the outside of the chamber 2. Likewise, also the fixed mass 4b can be biased at the voltage V1 by means of a respective electrical-contact terminal (not shown in FIG. 10), formed together with the electrical-contact terminal 11 shown in FIG. 10 and set outside the chamber 2.

The electrical-contact terminal at ground reference voltage set in a position corresponding to the side walls 2b has the function of enabling discharge of electrostatic voltage accumulated on the cap 49. However, said electrical-contact terminal at ground reference voltage is not necessary for the purposes of the present disclosure.

The manufacturing steps for producing the microfluidic device 10' of FIG. 4 or FIG. 5 are similar to the manufacturing steps of FIGS. 6-11 described previously.

It is evident that, according to the embodiment of FIG. 4 (or likewise FIG. 5), the mobile mass 4a is not formed, and hence the electrical-contact region 34b is not present either. In addition to the steps previously described, this embodiment envisages the step of forming the fixed electrode 21. This step is carried out together with the step of formation of the electrical-contact region 34a by depositing a layer of conductive material (here, doped polysilicon) in the regions where, in subsequent steps, it is desired to form the fixed mass 4b (in particular in a region of the wafer substantially aligned, along Z, to the suspended beams 9 of the fixed mass 4b, as shown in FIG. 4 and FIG. 5). Said layer of conductive material is, in particular, made of the same material used to form the electrical-contact region 34a, and is hence deposited and defined together with deposition and definition of the electrical-contact region 34a. The fixed electrode 21 thus formed is then coated with the insulating layer 35, which insulates it from the fluid and from the reagents present, in use, in the chamber 5.

From an examination of the characteristics of the disclosure provided according to the present disclosure the advantages that it affords are evident.

In particular, the present disclosure makes it possible to obtain a microfluidic device 10, 10' that is completely integrated, provided with one stirring structure 4 for each chamber 2, which can be actuated independently of the stirring structures 4 of the other chambers of the microfluidic device itself. Each reaction chamber 2 can hence be used independently of the other chambers.

Moreover, the manufacturing steps are of a standard type, both as regards the materials used and as regards the equipment used for manufacture, rendering the process compatible with current micromachining and micromanufacturing techniques, also in the electronic field. The same equipment can hence be re-used without any risk of contaminations.

From a functional standpoint, the present disclosure makes it possible to obtain in a simple and integrated way complete and fast solubilization of pre-charged solid reagents, thus overcoming the limits of current procedures, which envisage the use of external heat sources that increase the risk of a possible degradation of the reagents, in addition to requiring prolonged times for solubilization; said methods imply, moreover, the preference for additional heaters.

Finally, it is clear that modifications and variations may be made to what has been described and illustrated herein, without thereby departing from the sphere of protection of the present disclosure.

For example, the number of chambers 2 for each microfluidic device 10, 10' may be chosen according to the preferences, between one and any number.

Also the dimensions of each chamber 2 may be chosen freely, as likewise the dimensions of the stirring structure 4, compatibly with structural limits for guaranteeing strength of the stirring structure 4 in regard to external stresses (above all in the case of disposable portable devices).

Moreover, the driving unit 20, comprising one or more voltage power supplies, may be integrated in the substrate 30 of the microfluidic device 10, 10', in a way in itself known.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A microfluidic device comprising:
a semiconductor body having a first side and a second side;
a well in the semiconductor body at the first side, the well having a bottom surface, the well being configured to contain a fluid; and
a first stirring structure integrated in the well, the first stirring structure having a first base coupled to the bottom surface of the well and having a first plurality of beams cantilevered from the first base; and
an electrode in the bottom surface of the well, ends of the first plurality of beams that are distal from the first base overlapping the electrode, the first plurality of beams being configured to move in a direction that is substantially perpendicular to the bottom surface in response to a first voltage being applied to the electrode and a second voltage being applied to the first plurality of beams.

2. The microfluidic device according to claim 1, further comprising a second stirring structure having a second base and a second plurality of beams cantilevered from the second base, the second stirring structure being coupled to the semiconductor body.

3. The microfluidic device according to claim 2, wherein the first and second plurality of beams each have a longitudinal length extending in a plane, the first plurality of beams being arranged with respect to the second plurality of beams and form a comb-fingered structure.

4. The microfluidic device according to claim 1, wherein the first plurality of beams have a longitudinal length that extends above the bottom surface of the well.

5. The microfluidic device according to claim 1, further comprising:
first conductive strips in the semiconductor body above the bottom surface, the first conductive strips being electrically coupled to respective regions of the first base of the first stirring structure, the first conductive strips being configured to apply the second voltage to the first base.

6. The microfluidic device according to claim 5, further comprising:
first and second pillars, the first base being fixed with respect to the semiconductor body and being coupled to the semiconductor body by the first and second pillars; and
first conductive paths, the first and second pillars being coupled to the semiconductor body through a respective first conductive path.

7. The microfluidic device according to claim 1, further comprising a second stirring structure having a second base and a second plurality of beams cantilevered from the second base, the second plurality of beams being over the electrode.

8. A microfluidic device comprising:
a body having a first surface and a second surface;
a well configured to hold a fluid and formed in the first surface of the body, the well having a bottom surface;
a fixed mass fixedly coupled to the body;
elastic elements coupled to the body; and
a moveable mass located in the well and having a first base and a first plurality of beams extending from the first base, the moveable mass being coupled to the elastic elements, the moveable mass being configured to move relative to the body and in response to a bias between the fixed mass and the moveable mass, thereby agitating the fluid in the well.

9. The microfluidic device according to claim 8, wherein the fixed mass has a second base and a second plurality of beams extending from the second base, the moveable mass being configured to move in response to the second plurality of beams being biased relative to the first plurality of beams.

10. The microfluidic device according to claim 9, wherein the first and second plurality of beams are arranged comb-fingered with each other and are located in a plane that is substantially parallel with the first surface of the body.

11. The microfluidic device according to claim 8, wherein the body includes one of the following materials: plastic, glass, ceramic and semiconductor.

12. The microfluidic device according to claim 8, wherein the fixed mass has a second base and a second plurality of beams extending from the second base, the second base being coupled to the bottom surface of the well.

13. The microfluidic device according to claim 8, wherein the well has a side surface, the fixed mass being spaced from the side surface.

14. The microfluidic device according to claim 8, wherein the moveable mass is suspended in the well by the elastic elements.

15. The microfluidic device according to claim 1, wherein the well has a side surface, the first stirring structure is spaced from the side surface of the well.

16. A semiconductor device, comprising:
a semiconductor substrate;
a well formed in the semiconductor substrate, the well having a bottom surface;
a fixed stirring structure positioned in the well, the fixed stirring structure having a first base and a first plurality of beams extending from the first base; and
a moveable stirring structure positioned in the well, the moveable stirring structure having a second base and a second plurality of beams extending from the second base in a first direction, the second base and the second plurality of beams configured to move in a second direction that is substantially the first direction.

17. The semiconductor device of claim 16, wherein a beam of the second plurality of beams is inserted between two beams of the first plurality of beams in response to the moveable stirring structure being moved.

18. The semiconductor device of claim 16, wherein a beam of the second plurality of beams is at least partially inserted between two beams of the first plurality of beams.

19. The semiconductor device of claim 16, further comprising:
a plurality of pillars, the fixed stirring structure being coupled to the semiconductor substrate by the plurality of pillars; and
elastic elements, the moveable stirring structure being coupled to the semiconductor substrate by the elastic elements.

20. The semiconductor device of claim 19, further comprising:
a first electrode, the fixed stirring structure being electrically coupled to the first electrode through the plurality of pillars; and
a second electrode, the moveable stirring structure being electrically coupled to the second electrode through the elastic elements.

* * * * *